US00PP19751P2

(12) United States Plant Patent
van der Helm

(10) Patent No.: US PP19,751 P2
(45) Date of Patent: Feb. 17, 2009

(54) CARNATION PLANT NAMED 'KOBIANCA'

(50) Latin Name: *Dianthus caryophyllus*
Varietal Denomination: Kobianca

(75) Inventor: Franciscus Jacobus Joseph van der Helm, Aalsmeer (NL)

(73) Assignee: Kooij & Zonen B.V., Aalsmeer (NL)

( * ) Notice: Subject to any disclaimer, the term of this patent is extended or adjusted under 35 U.S.C. 154(b) by 0 days.

(21) Appl. No.: 12/069,039

(22) Filed: Feb. 6, 2008

(51) Int. Cl.
*A01H 5/00* (2006.01)

(52) U.S. Cl. ..... Plt./272
(58) Field of Classification Search ..... Plt./272
See application file for complete search history.

(56) References Cited

PUBLICATIONS

UPROV–ROM GTITM, Plant Variety Database, 2008/01, GTI Jouve Retrieval Software, citation for 'Bianca'.*

* cited by examiner

*Primary Examiner*—Annette H Para
*Assistant Examiner*—S. B. McCormick

(57) ABSTRACT

A new and distinct cultivar of Carnation plant named 'Kobianca', characterized by its compact, upright, somewhat outwardly spreading and mounded plant habit; moderately vigorous growth habit; freely branching habit; numerous double red purple and white bi-colored that are positioned above and beyond the foliage; and good flower longevity.

1 Drawing Sheet

Botanical designation: *Dianthus caryophyllus.*
Cultivar denomination: 'Kobianca'.

BACKGROUND OF THE INVENTION

The present invention relates to a new and distinct cultivar of Carnation plant, botanically known as *Dianthus caryophyllus,* grown as a potted plant, and hereinafter referred to by the name 'Kobianca'.

The new Carnation is a product of a planned breeding program conducted by the Inventor in Aalsmeer, The Netherlands. The objective of the breeding program was to develop new freely-branching Carnation cultivars with numerous flowers and attractive flower coloration.

The new Carnation originated from a cross-pollination made by the Inventor in July, 2002, of a proprietary selection of *Dianthus caryophyllus* identified as code number 200376, not patented, as the female, or seed, parent with a proprietary selection of *Dianthus caryophyllus* identified as code number 996355, not patented, as the male, or pollen, parent. The cultivar Kobianca was discovered and selected by the Inventor as a flowering plant within the progeny of the stated cross-pollination in a controlled environment in Aalsmeer, The Netherlands.

Asexual reproduction of the new cultivar by terminal cuttings propagated in a controlled environment in Aalsmeer, The Netherlands since 2002, has shown that the unique features of this new Carnation are stable and reproduced true to type in successive generations of asexual reproduction.

SUMMARY OF THE INVENTION

The cultivar Kobianca has not been observed under all possible environmental conditions. The phenotype may vary somewhat with variations in environment such as temperature and light intensity, without, however, any variance in genotype.

The following traits have been repeatedly observed and are determined to be the unique characteristics of 'Kobianca'. These characteristics in combination distinguish 'Kobianca' as a new and distinct cultivar of Carnation:

1. Compact, upright, somewhat outwardly spreading and mounded plant habit.
2. Moderately vigorous growth habit.
3. Freely branching habit.
4. Numerous double red purple and white bi-colored that are positioned above and beyond the foliage.
5. Good flower longevity.

Plants of the new Carnation differ from plants of the parent selections primarily in flower color. In addition, plants of the new Carnation differ from plants of the parent selections in growth habit as plants of the new Carnation are more compact than plants of the parent selections.

Plants of the new Carnation can be compared to plants of the Carnation cultivar Margarita, disclosed in U.S. Plant Pat. No. 17,335. In side-by-side comparisons conducted in Aalsmeer, The Netherlands, plants of the new Carnation differed from plants of the cultivar Margarita in the following characteristics:

1. Plants of the new Carnation were more compact than plants of the cultivar Margarita.
2. Plants of the new Carnation were more freely branching than plants of the cultivar Margarita.
3. Plants of the new Carnation had shorter leaves than plants of the cultivar Margarita.
4. Flowers of plants of the new Carnation had more petals than flowers of plants of the cultivar Margarita.
5. Petals of plants of the new Carnation had entire margins whereas petals of plants of the cultivar Margarita had serrated margins.
6. Flowers of plants of the new Carnation were more intense in color than flowers of plants of the cultivar Margarita.

BRIEF DESCRIPTION OF THE PHOTOGRAPH

The accompanying photograph illustrates the overall appearance of the new Carnation. This photograph shows the colors as true as it is reasonably possible to obtain in colored reproductions of this type. Colors in the photograph may differ slightly from the color values cited in the detailed botanical description which accurately describe the colors of the new Carnation. The photograph comprises a side perspective view of a typical flowering plant of 'Kobianca' grown in a container.

DETAILED BOTANICAL DESCRIPTION

In the following description, color references are made to The Royal Horticultural Society Colour Chart, 1995 Edition, except where general terms of ordinary dictionary significance are used. Measurements and numerical values represent averages for typical flowering plants. The aforementioned photograph and following observations and measurements describe plants grown in Aalsmeer, The Netherlands during the spring in a glass-covered greenhouse and under conditions and practices which approximate those generally used in commercial potted Carnation production. During the production of the plants, day temperatures ranged from 15° C. to 25° C. and night temperatures ranged from 10° C. to 12° C. Single plants were grown in 10-cm pots and were pinched one time. Plants were about four months old when the photograph and the detailed description were taken.

Botanical classification: *Dianthus caryophyllus* cultivar Kobianca.

Parentage:

*Female, or seed, parent.*—Proprietary selection of *Dianthus caryophyllus* identified as code number 200376, not patented.

*Male, or pollen, parent.*—Proprietary selection of *Dianthus caryophyllus* identified as code number 996355, not patented.

Propagation:

*Type.*—Terminal cuttings.

*Time to initiate roots, summer.*—About ten days at 20° C. to 25° C.

*Time to initiate roots, winter.*—About twelve days at 20° C.

*Time to produce a rooted young plant, summer.*—About 25 days at 20° C. to 25° C.

*Time to produce a rooted young plant, winter.*—About 30 days at 20° C.

*Root description.*—Fine, fibrous; white in color.

*Rooting habit.*—Freely branching.

Plant description:

*Plant form.*—Compact, upright, somewhat outwardly spreading and mounded plant habit; inverted triangle.

*Growth and branching habit.*—Moderately vigorous and freely-branching growth habit with about ten primary lateral branches; dense and bushy growth habit. Pinching, that is removal of the terminal apex, enhances lateral branching.

*Plant height.*—About 15 cm.

*Plant diameter or spread.*—About 17 cm.

*Lateral branches.*—Length: About 14 cm. Diameter: About 3 mm. Internode length: About 3 cm. Texture: Smooth, glabrous. Color: 137B.

*Foliage description.*—Arrangement: Opposite, simple; sessile. Length: About 6.6 cm. Width: About 8 mm. Shape: Lanceolate. Apex: Acute. Base: Truncate. Margin: Entire. Texture, upper and lower surfaces: Smooth, glabrous. Venation pattern: Pinnate. Color: Developing foliage, upper and lower surfaces: 135A. Fully expanded foliage, upper and lower surfaces: 137A; venation, 137A.

*Flower description.*—Flower type and habit: Double flowers. Freely flowering habit; usually three to four open flowers per lateral branch. Flowers positioned above and beyond the foliage; typically facing upright. Flowers persistent. Flowers faintly fragrant; clove-like. Natural flowering season: Flowering is continuous through the summer in The Netherlands. Plants begin flowering about three months after planting. Flowers last about ten days on the plant. Flowers persistent. Flower diameter: About 3.6 cm. Flower depth: About 1.7 cm. Flower buds: Length: About 1.9 cm. Diameter: About 8 mm. Shape: Obovate. Color: 138A. Petals/petaloids: Quantity/arrangement: About 29 per flower in several whorls. Length, outer petals: About 3.2 cm. Width, outer petals: About 1.9 cm. Shape: Roughly spatulate. Apex: Emarginate. Base: Acute. Margin: Serrated. Texture, upper and lower surfaces: Smooth, glabrous. Color: When opening and fully opened, upper surface: 60A, towards the margin, close to 155D. When opening and fully opened, lower surface: Close to 155D. Sepals: Quantity/arrangement: Two fused in a single whorl. Length: About 1.7 cm. Width: About 4 mm. Shape: Narrowly deltoid. Apex: Acute. Margin: Entire. Texture, upper and lower surfaces: Smooth, glabrous. Color, upper and lower surfaces: 137A. Peduncles: Length: About 1.5 mm. Diameter: About 2 mm. Strength: Moderately strong. Texture: Smooth, glabrous. Color: 139B. Reproductive organs: Stamens: Quantity: About five per flower. Anther length: About 2 mm. Anther shape: Oblong. Anther color: 59B. Pollen amount: Scarce. Pistils: Quantity: One per flower. Pistil length: About 1.1 cm. Stigma shape: Curled. Stigma color: 70A flushed with close to 155D. Style length: About 1 cm. Style color: 70A flushed with close to 155D. Ovary color: 145C. Seeds: Quantity: Five per capsule. Length: About 2.5 mm. Diameter: About 2.5 mm. Color: Close to 202A.

Disease/pest resistance: Plants of the new Carnation have not been observed to be resistant to pathogens and pests common Carnations.

Temperature tolerance: Plants of the new Carnation have been observed to tolerate temperatures ranging from about −5° C. to 40° C.

It is claimed:

1. A new and distinct Carnation plant named 'Kobianca' as illustrated and described.

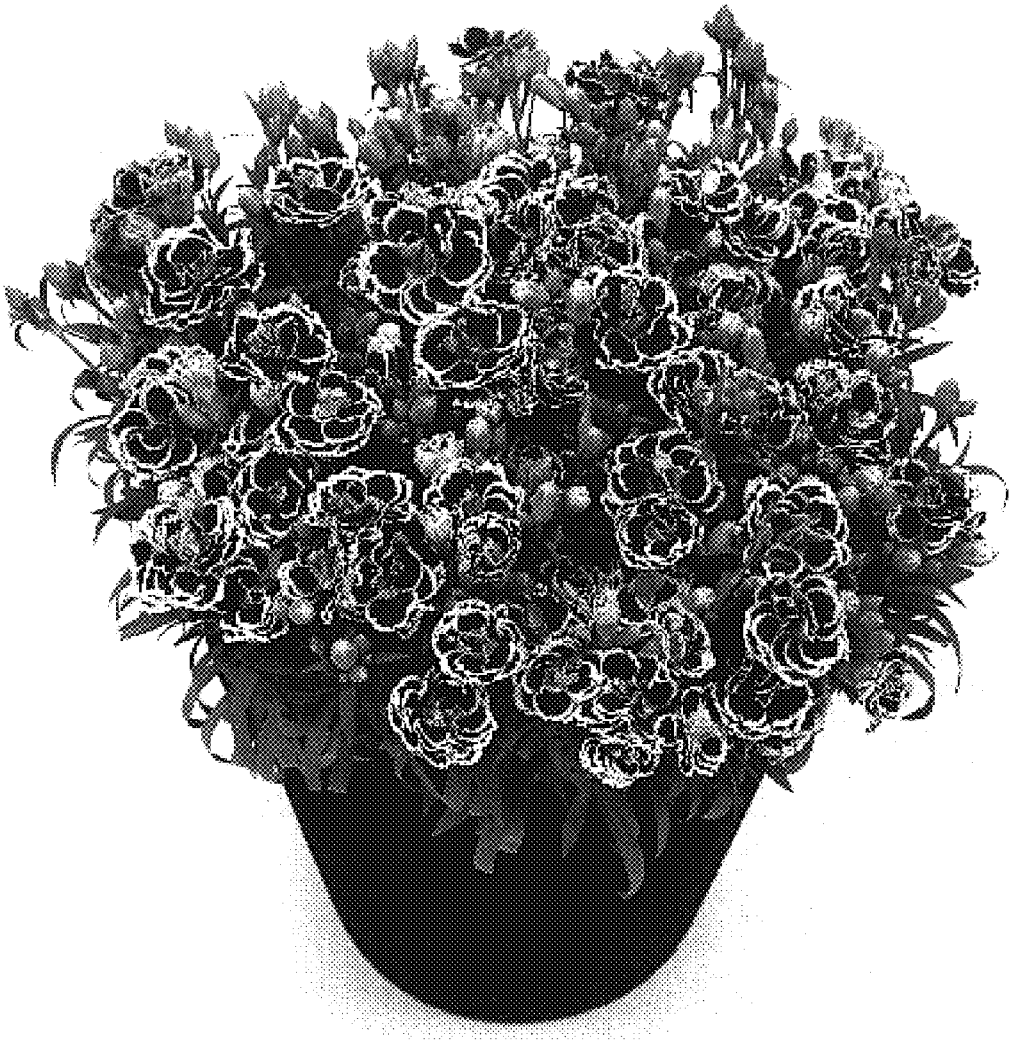

* * * * *